US005965534A

United States Patent [19]
Pang et al.

[11] Patent Number: 5,965,534
[45] Date of Patent: Oct. 12, 1999

[54] USE OF ω-CONOTOXIN ANALOGS FOR TREATING RETINAL AND OPTIC NERVE HEAD DAMAGE

[75] Inventors: Iok-Hou Pang, Grand Prairie; Michael Kapin; Mark Hellberg, both of Arlington, all of Tex.

[73] Assignee: Alcon Laboratories, Inc., Fort Worth, Tex.

[21] Appl. No.: 09/039,168

[22] Filed: Mar. 13, 1998

Related U.S. Application Data

[63] Continuation of application No. 08/562,142, Nov. 22, 1995, abandoned.

[51] Int. Cl.$^6$ ..................................................... A61K 38/00
[52] U.S. Cl. .............................. 514/12; 514/13; 514/912; 530/324; 530/325; 530/857; 424/78.04; 424/427
[58] Field of Search ..................................... 530/324, 325, 530/857; 514/12, 13, 912; 424/78.04, 427

[56] References Cited

U.S. PATENT DOCUMENTS

| | | | |
|---|---|---|---|
| 4,447,356 | 5/1984 | Olivera et al. | 260/112.5 R |
| 4,550,022 | 10/1985 | Garabedian et al. | 424/127 |
| 4,950,739 | 8/1990 | Cherksey et al. | 530/350 |
| 5,051,403 | 9/1991 | Miljanich et al. | 514/12 |
| 5,189,020 | 2/1993 | Miljanich et al. | 514/12 |
| 5,432,155 | 7/1995 | Olivera et al. | 514/12 |

FOREIGN PATENT DOCUMENTS

| | | |
|---|---|---|
| 9107980 | 6/1991 | WIPO . |
| WO 91/07980 | 6/1991 | WIPO . |
| 9310145 | 5/1993 | WIPO . |
| WO 93/10145 | 5/1993 | WIPO . |
| WO 93/13128 | 7/1993 | WIPO . |
| WO 94/13275 | 6/1994 | WIPO . |
| WO 95/11256 | 4/1995 | WIPO . |

OTHER PUBLICATIONS

Benveniste, "Elevation of the Extracellular Concentrations of Glutamate and Asparate in Rat Hippocampus During Transient Cerebral Ishcemia Monitored by Intracerebral Microdialysis", *Journal of Neurochemistry*, vol. 43, No. 5, pp. 1369–1374 (1984).
Choi, D., et al.; "Excitotoxic Cell Death", *Journal of Neurobiology*, vol. 23, No. 9, pp. 1261–1276 (1992).
Choi, D.; "Glutamate Neurotoxicity and Diseases of the Nervous System", *Neuron*, vol. 1, pp. 623–634 (1988).
Cruz, L., et al.; "Characterization of the ω–Conotoxin Target. Evidence for Tissue–Specific Heterogeneity in Calcium Channel Types", *Biochemistry*, vol. 26, pp. 820–824 (1987).
Cruz, L., et al.; "Conus Venoms: A Rich Source of Neuroactive Peptides", *J. Toxicol.–Toxin Reviews*, vol. 4, No. 2, pp. 107–132 (1985).
David, P., et al.; "Involvement of Excitatory Neurotransmitters in the Damage Produced in Chick Embryo Retinas by Anoxia and Extracellular High Potassium", *Exp. Eye Res.*, vol. 46, pp. 657–662 (1988).

Deshpande, J., et al.; "Flunarizine, a Calcium Entry Blocker, Ameliorates Ischemic Brain Damage in the Rat", *Anesthesiology*, vol. 64, No. 2, pp. 215–224 (1986).
Jones, O., et al.; "Localization and Mobility of ω–Conotoxin—Sensitive $Ca^{2+}$Channels in Hippocampal CA1 Neurons", *Science*, vol. 244, pp. 1189–1193 (1989).
McCleskey, E., et al.; "ω–Conotoxin: Direct and persistent blockafe of specific types of calcium channels in neurons but not muscle", *Proc. Natl. Acad. Sci. USA*, vol. 84, pp. 4327–4331 (1987).
Olney, J., et al.; "The Role of Specific Ions In Glutamate Neurotoxicity", *Neuroscience Letters*, vol. 65, pp. 65–71 (1986).
Reynolds, I., et al.; "Brain voltage–sensitive calcium channel subtypes differentiated by ω–conotoxin fraction GVIA", *Proc. Natl. Acad. Sci. USA*, vol. 83, pp. 8804–8807 (1986).
Sauter, A., et al.; "Treatment of Hypertension with Isradipine Reduces Infarct Size following Stroke in Laboratory Animals", *The American Journal of Medicine*, vol. 86 (suppl 4A), pp. 130–133 (1989).
Scatton, B., et al.; "Eliprodil Hydrochloride", *Drugs of the Future*, vol. 19, No. 10, pp. 905–909 (1994).
Sheardown, M., et al.; "2,3–Dihydroxy–6–nitro–7–sulfamoyl–benzo(F)quinoxaline: A Neuroprotectant for Cerebral Ischemia", *Science*, vol. 247, pp. 571–574 (1990).
Sher, E. et al.; "ω–Conotoxin binding and effects on calcium channel function in human neuroblastoma and rat pheochromocytoma cell lines", *FEBS Letters*, vol. 235, No. 1,2, pp. 178–182 (1988).
Siesjö, "Calcium, Excitotoxins, and Brain Damage", *NIPS*, vol. 5, pp. 120–124 (1990).
Siliprandi, R., et al.; "N–methyl–D–asparate–induced neurotoxicity in the adult rat retina", *Visual Neuroscience*, vol. 8, pp. 567–573 (1992).
Sisk, D., et al.; "Histologic changes in the inner retina of albino rates following intravitreal injection of monosodium L–glutamate", *Graefe's Arch Clin Exp Ophthalmol*, vol. 223, pp. 250–258 (1985).
Smith, M., et al.; "Postischemic treatment with the Ω–conopeptide SNX 111 protects the rat brain against ischemic damage", J. Krieglstein, H. Oberpichler–Schwenk (Eds.) Pharmacology of Cerebral Ischemia, pp. 161–166 (1992).
Sucher, N. et al.; "N–methyl–D–asparate Antagonists Prevent Kainate Neurotoxicity in Rat Retinal Ganglion Cells in vitro", *The Journal of Neuroscience*, vol. 11, No. 4, pp. 966–971 (1991).
Tung, N., et al.; "A quantitative analysis of the effects of excitatory neurotoxins on retinal ganglion cells in the chick", *Visual Neuroscience*, vol. 4, pp. 217–223 (1990).
Valentino, K., et al.; "A selective N–type calcium channel antagonist protects against neuronal loss after global cerebral ischemia", *Proc. Natl. Acad. Sci. USA*, vol. 90, pp. 7894–7897 (1993).

*Primary Examiner*—Cecilia J. Tsang
*Assistant Examiner*—C. Delacroix-Muirheid
*Attorney, Agent, or Firm*—Michael C. Mayo

[57] ABSTRACT

The invention is directed to the use of ω-conotoxins for the prevention and treatment of retinal or optic nerve head damage in humans. Compositions and methods are disclosed.

9 Claims, No Drawings ial Ophthalmology, volume 223, pages 250–258 (1985);

```
                          SEQUENCE LISTING (1) GENERAL INFORMATION:

(iii) NUMBER OF SEQUENCES:  7

(2) INFORMATION FOR SEQ ID NO:  1:

(i) SEQUENCE CHARACTERISTICS:
         (A) LENGTH:  25 amino acids
         (B) TYPE:  amino acid
         (C) STRANDEDNESS:
         (D) TOPOLOGY:  unknown (ii) MOLECULE TYPE:
         (A) DESCRIPTION:  peptide (iii) HYPOTHETICAL:  No (iv) ANTI-SENSE:  No (xi) SEQUENCE DESCRIPTION:  SEQ ID NO:  1:

Cys Lys Gly Lys Gly Ala Lys Cys Ser Arg Leu Met Tyr Asp Cys Cys Thr
1               5                  10                  15

Gly Ser Cys Arg Ser Gly Lys Cys
           20                  25

(2) INFORMATION FOR SEQ ID NO:  2:

(i) SEQUENCE CHARACTERISTICS:
         (A) LENGTH:  25 amino acids
         (B) TYPE:  amino acid
         (C) STRANDEDNESS:
         (D) TOPOLOGY:  unknown (ii) MOLECULE TYPE:
         (A) DESCRIPTION:  peptide (iii) HYPOTHETICAL:  No (iv) ANTI-SENSE:  No (xi) SEQUENCE DESCRIPTION:  SEQ ID NO:  2:

Cys Lys Gly Lys Gly Ala Ser Cys His Arg Thr Ser Tyr Asp Cys Cys Thr
1               5                  10                  15

Gly Ser Cys Asn Arg Gly Lys Cys
           20                  25

(2) INFORMATION FOR SEQ ID NO:  3:

(i) SEQUENCE CHARACTERISTICS:
         (A) LENGTH:  27 amino acids
         (B) TYPE:  amino acid
         (C) STRANDEDNESS:
         (D) TOPOLOGY:  unknown (ii) MOLECULE TYPE:
         (A) DESCRIPTION:  peptide (iii) HYPOTHETICAL:  No (iv) ANTI-SENSE:  No (xi) SEQUENCE DESCRIPTION:  SEQ ID NO:  3:
```

```
Cys Lys Ser Xaa Gly Ser Ser Cys Ser Xaa Thr Ser Tyr Asn Cys Cys Arg
1               5                   10                  15

Ser Cys Asn Xaa Tyr Thr Lys Arg Cys Tyr
            20                  25
```

(2) INFORMATION FOR SEQ ID NO: 4:

(i) SEQUENCE CHARACTERISTICS:
        (A) LENGTH:  29 amino acids
        (B) TYPE:  amino acid
        (C) STRANDEDNESS:
        (D) TOPOLOGY:  unknown (ii) MOLECULE TYPE:
        (A) DESCRIPTION:  peptide (iii) HYPOTHETICAL:  No (iv) ANTI-SENSE:  No (xi) SEQUENCE DESCRIPTION:  SEQ ID NO:  4:

```
Cys Lys Ser Xaa Gly Thr Xaa Cys Ser Arg Gly Met Arg Asp Cys Cys Thr
1               5                   10                  15

Ser Cys Leu Leu Tyr Ser Asn Lys Cys Arg Arg Tyr
            20                  25
```

(2) INFORMATION FOR SEQ ID NO: 5:

(i) SEQUENCE CHARACTERISTICS:
        (A) LENGTH:  27 amino acids
        (B) TYPE:  amino acid
        (C) STRANDEDNESS:
        (D) TOPOLOGY:  unknown (ii) MOLECULE TYPE:
        (A) DESCRIPTION:  peptide (iii) HYPOTHETICAL:  No (iv) ANTI-SENSE:  No (xi) SEQUENCE DESCRIPTION:  SEQ ID NO:  5:

```
Cys Lys Pro Xaa Gly Ser Xaa Cys Arg Val Ser Ser Tyr Asn Cys Cys Ser
1               5                   10                  15

Ser Cys Lys Ser Tyr Asn Lys Lys Cys Gly
            20                  25
```

(2) INFORMATION FOR SEQ ID NO: 6:

(i) SEQUENCE CHARACTERISTICS:
        (A) LENGTH:  24 amino acids
        (B) TYPE:  amino acid
        (C) STRANDEDNESS:
        (D) TOPOLOGY:  unknown (ii) MOLECULE TYPE:
        (A) DESCRIPTION:  peptide (iii) HYPOTHETICAL:  No (iv) ANTI-SENSE:  No (xi) SEQUENCE DESCRIPTION:  SEQ ID NO:  6:

```
Cys Arg Ser Ser Gly Ser Xaa Cys Gly Val Thr Ser Ile Cys Cys Gly Arg
1               5                   10                  15

Cys Tyr Arg Gly Lys Cys Thr
            20
```

(2) INFORMATION FOR SEQ ID NO: 7:

```
    (i) SEQUENCE CHARACTERISTICS:
        (A) LENGTH:  27 amino acids
        (B) TYPE:  amino acid
        (C) STRANDEDNESS:
        (D) TOPOLOGY:  unknown (ii) MOLECULE TYPE:
        (A) DESCRIPTION:  peptide (iii) HYPOTHETICAL:  No (iv) ANTI-SENSE:  No (xi) SEQUENCE DESCRIPTION: SEQ ID NO:  7:

Cys Leu Ser Xaa Gly Ser Ser Cys Ser Xaa Thr Ser Tyr Asn Cys Cys Arg
1               5                   10                  15

Ser Cys Asn Xaa Tyr Ser Arg Lys Cys Arg
            20                  25
```

USE OF ω-CONOTOXIN ANALOGS FOR TREATING RETINAL AND OPTIC NERVE HEAD DAMAGE This application is a continuation of U.S. patent application Ser. No. 08/562,142 filed Nov. 22, 1995, now abandoned.

The present invention relates to peptides useful in the prevention or treatment of retinal and optic nerve head damage. In particular, the peptides used in compositions and methods of the present invention are ω-conotoxin analogs.

BACKGROUND OF THE INVENTION

Acute retinal or optic nerve head damage, which can result in the loss of vision, is caused by trauma and various pathological events such as ischemia, hypoxia, or edema.

Retinal or optic nerve head ischemia or hypoxia results when blood supply is significantly reduced to these tissues. Ischemia is a complex pathological episode involving numerous biochemical events. In recent years, the involvement of excitatory amino acids in ischemia-related neuronal and retinal damage has been implicated. (See Choi, Excitatory cell death, *Journal of Neurobiology,* volume 23, pages 1261–1276 (1992); Tung et al., A quantitative analysis of the effects of excitatory neurotoxins on retinal ganglion cells in the chick, *Visual Neuroscience,* volume 4, pages 217–223 (1990); Sisk et al., Histologic changes in the inner retina of albino rats following intravitreal injection of monosodium L-glutamate, *Graefe's Archive for Clinical and Experimental Ophthalmology,* volume 223, pages 250–258 (1985); Siliprandi et al., N-methyl-D-aspartate-induced neurotoxicity in the adult rat retina, *Visual Neuroscience,* volume 8, pages 567–573 (1992); and David et al., Involvement of excitatory neurotransmitters in the damage produced in chick embryo retinas by anoxia and extracellular high potassium, *Experimental Eye Research,* volume 46, pages 657–662 (1988)) During ischemia or hypoxia, excitatory amino acids are markedly elevated (Benveniste et al, Elevation of the extracellular concentrations of glutamate and aspartate in rat hippocampus during transient cerebral ischemia monitored by intracerebral microdialysis, *Journal of Neurochemistry,* volume 43, pages 1369–1374 (1984)), the consequences of which may lead to excessive stimulation of post-synaptic excitatory amino acid receptors, and potentially resulting in cell injury. Antagonists against excitatory amino acid receptors have been shown to reduce neuronal and retinal damage in ischemic conditions. (See Sheardown et al., 2,3-Dihydorxy-6-nitro-7-sulfamoyl-benzo (F)quinoxaline: a neuroprotectant for cerebral ischemia, *Science,* volume 247, pages 571–574 (1990); Scatton et al., Eliprodil Hydrochloride, *Drugs of the Future,* volume 19, pages 905–909 (1994); and Sucher et al., N-methyl-D-aspartate antagonists prevent kainate neurotoxicity in rat retinal ganglion cells in vitro, *Journal of Neuroscience,* volume 11, pages 966–971 (1991)). Release of excitatory amino acids has been demonstrated to cause cytotoxicity due to increases in intracellular calcium levels, which in turn affects protein phosphorylation, proteolysis, lipolysis, and ultimately causing cell death. (See Choi, Glutamate neurotoxicity and diseases of the nervous system, *Neuron,* volume 1, pages 623–634 (1988); Siesjo, Calcium, excitotoxins, and brain damage, *NIPS,* volume 5, pages 120–125 (1990) and Olney et al., The role of specific ions in glutamate neurotoxicity, *Neuroscience Letters,* volume 65, pages 65–71 (1986)). The elevation of intracellular levels of calcium occurs in part by excitatory amino acid-induced depolarization of the cell membrane and subsequent activation of post-synaptic voltage-dependent calcium channels.

Hence, inhibitors of post-synaptic voltage-dependent calcium channels including the dihydropyridines, such as nitrendipine and nifedipine; the phenylalkylamines, such as verapamil, the diphenylalkylamines, such as flunarizine; and the benzothiazepines, such as diltiazem, were also effective in the protection of neuronal damage after ischemia (Deshpande et al., Flunarizine, a calcium entry blocker, ameliorates ischemic brain damage in the rat, *Anethesiology,* volume 64, pages 215–224 (1986); and Sauter et al., Treatment of hypertension with isradipine reduces infarct size following stroke in laboratory animals, *American Journal of Medicine,* volume 86, pages 130–133 (1989)). Unfortunately, these same agents may block voltage-dependent calcium channels in vascular smooth muscles, potentially leading to vasodilation and possibly systemic hypotension.

A new development in the treatment of ischemia-induced neuronal damage is to minimize the release of excitatory amino acids from the pre-synaptic nerve terminal. This release is dependent upon an elevation of calcium in the nerve terminal. The pre-synaptic calcium influx into neuronal tissues is believed to be mediated by the N-type calcium channel, which can be selectively inhibited by ω-conotoxins (Reynolds et al., Brain voltage sensitive calcium channel subtypes differentiated by ω-conotoxin fraction GVIA, *Proceedings of the National Academy of Science, USA,* volume 83, pages 8804–8807 (1986); and McCleskey et al., ω-Conotoxin: Direct and persistant blockade of specific types of calcium channels in neurons but not muscle, *Proceedings of the National Academy of Science, USA,* volume 84, pages 4327–4331 (1987)). Indeed, treatment of animals with ω-conotoxins protects them against ischemic damage (Smith et al., Postischemic treatment with the ω-conopeptide SNX 111 protects the rat brain against ischemic damage, *Fourth International Symposium in Pharmacology of Cerebral Ischemia,* volume 36, pages 161–166 (1992); and Valentino et al., A selective N-type calcium channel antagonist protects against neuronal loss after global cerebral ischemia, *Proceedings of the National Academy of Science, USA,* volume 90, pages 7894–7897 (1993)).

The conotoxins are a class of small peptides derived from the molusk genus Conus. Over 500 species of this genus have been reported to exist (U.S. Pat. No. 5,432,155, Olivera et al.). The conotoxins of the *C. geographus* and *C. magus* species have been particularly studied. The conotoxins are further classified by their biological activity. For example, α-conotoxins block the nictotinic acetylcholine receptor, μ-conotoxins block skeletal muscle sodium channels, and ω-conotoxins block pre-synaptic neuronal calcium channels (Cruz, Conus Venoms: A Rich Source of Neuroactive Peptides, *Journal of Toxicology and Toxin Review,* volume 4, pages 107–132 (1985)).

ω-conotoxins have been researched extensively in the area of N-type pre-synaptic voltage activated calcium channels. These channels are distributed predominantly in neuronal cells. The following publications may be referred to for further background and characterization of the effects of ω-conotoxins on voltage activated calcium channels in neuronal tissue:

Sher et al., ω-Conotoxin Binding and Effects on Calcium Channel Function in Human Neuroblastoma and Rat Pheochromocytoma Cell Lines, *FEBS Letters,* volume 235, number 1,2, pages 178–182(1988);

Cruz et al., Characterization of the ω-Conotoxin Target. Evidence For Tissue-Specific Hetereogeneity in Calcium Channel Types, *Biochemistry,* volume 26, pages 820–824 (1987); and Jones et al., Localization and Mobility of ω-conotoxin-Sensitive $Ca^{2+}$ Channels in Hippocampal CA1 Neurons, Science, volume 244, pages 1189–1193 (1989).

At least 11 homologous ω-conotoxins have been discovered. A number of publications disclose these conotoxins including: WIPO Publication No. WO 93/13128, for use as cerebral analgesics; U.S. Pat. No. 5,189,020 (Miljanich et al.), for brain ischemia therapy; and 4,950,739 (Cherksey et al.), for use as agents for blocking, isolating and purifying of calcium channels. Nowhere in the art, however, has it been proposed to acutely administer ω-conotoxins to prevent or ameliorate retinal or optic nerve head damage.

SUMMARY OF THE INVENTION

The present invention is directed to compositions and methods for preventing or treating retinal and/or optic nerve head injury as a consequence of ischemia or trauma.

In particular, the present invention provides compositions containing ω-conotoxins and methods of their use for the acute treatment of ocular neuronal tissues.

DETAILED DESCRIPTION OF THE INVENTION

The present invention provides compositions containing ω-conotoxin analogs and methods of use in treating acute retinal or optic nerve head damage. A number of ω-conotoxins have been isolated thus far, of which six may be included in compositions of the present invention. The primary structures of these six ω-conotoxins are listed in Table 1:

TABLE 1

1) OCT MVIIA (SEQ ID NO 1):

```
    1   2   3   4   5   6   7   8   9  10  11  12  13  14  15  16  17
    Cys-Lys-Gly-Lys-Gly-Ala-Lys-Cys-Ser-Arg-Leu-Met-Tyr-Asp-Cys-Cys-Thr- 18  19  20   21  22   23  24  25  26   27  28
   -Gly-Ser-Cys- -- -Arg- -- -Ser-Gly-Lys- -- -Cys
```

2) OCT MVIIB (SEQ ID NO 2):

```
    1   2   3   4   5   6   7   8   9  10  11  12  13  14  15  16  17
    Cys-Lys-Gly-Lys-Gly-Ala-Ser-Cys-His-Arg-Thr-Ser-Tyr-Asp-Cys-Cys-Thr- 18  19  20  21  22   23    24   25  26  27  28
   -Gly-Ser-Cys-Asg-Arg- ---  -  --- -Gly-Lys- --- -Cys
```

3) OCT GVIA (SEQ ID NO 3):

```
    1   2   3   4   5   6   7   8   9  10  11  12  13  14  15  16  17
    Cys-Lys-Ser-Xaa-Gly-Ser-Ser-Cys-Ser-Xaa-Thr-Ser-Tyr-Asg-Cys-Cys-Arg- 18   19  20  21  22  23  24   25   26  27  28   29     30   31
     - --- -Ser-Cys-Asg-Xaa-Tyr-Thr- --- -Lys-Arg-Cys- --- - --- -Tyr
```

4) OCT GVIIA (SEQ ID NO 4):

```
    1   2   3   4   5   6   7   8   9  10  11  12  13  14  15  16  17
    Cys-Lys-Ser-Xaa-Gly-Thr-Xaa-Cys-Ser-Arg-Gly-Met-Arg-Asp-Cys-Cys-Thr- 18    19  20  21  22  23  24  25  26   27  28  29 30  31
    - ---  --Ser-Cys-Leu-Leu-Tyr-Ser-Asg-Lys- --- -Cys-Arg-Arg-Tyr
```

5) OCT RVIA (SEQ ID NO 5):

```
    1   2   3   4   5   6   7   8   9  10  11  12  13  14  15  16  17
    Cys-Lys-Pro-Xaa-Gly-Ser-Xaa-Cys-Arg-Val-Ser-Ser-Tyr-Asg-Cys-Cys-Ser- 18   19  20  21  22  23  24   25   26  27  28  29
     - --- -Ser-Cys-Lys-Ser-Tyr-Asg- --- -Lys-Lys-Cys-Gly
```

6) OCT TVIA (SEQ ID NO 6):

```
    1   2   3   4   5   6   7   8   9  10  11  12  13  14  15  16  17
    Cys-Leu-Ser-Xaa-Gly-Ser-Ser-Cys-Ser-Xaa-Thr-Ser-Tyr-Asg-Cys-Cys-Arg- 18   19  20  21  22  23  24   25   26  27  28  29
     - --- -Ser-Cys-Asg-Xaa-Tyr-Ser- --- -Arg-Lys-Cys-Arg
``` wherein: Xaa is 4Hyp (4-hydroxyproline). As used herein, the term "ω-conotoxin" or "OCT peptide" refers to any of the six SEQ ID NOs 1–6 above, or analogs thereof, as defined below.

Certain criteria for permissible modifications and secondary structure requirements of the ω-conotoxins of the present invention have been set forth in U.S. Pat. No. 5,051,403 (Miljanich et al.) and U.S. Pat. No. 5,189,020 (Miljanich et al.), the entire contents of which, are incorporated herein by reference. In general, the natural OCT peptides are grouped into two groups, each with internal homologies distinct to that group, as can be appreciated from Table 1. The two groups are designated "M", including the MVIIA, and MVIIB, peptides, and "G," including the GVIA, GVIIA, RVIA, and TVIA peptides.

The two groups of OCT peptides are arranged in Table 1 with their six Cys residues aligned, which places these residues at positions 1, 8, 15, 16, 20, and 28. To make this alignment, a gap was introduced at the 18 position of the G-group peptides, and at the 23 and 27 positions of the M-group peptides. In the analysis below, these gaps retain the assigned number shown in Table 1, even though they represent amino acid deletions in the respective groups of active OCT peptides. The ω-conotoxins of the present invention are further defined by the following constraints:

1. The peptides in both groups include Cys residues at position 1, 8, 15, 16, 20, and 28. Other Cys residues may be substituted at the positions indicated below only if they are selectively protected during oxidation of the peptide to form the three disulfide linkages.

2. The peptides in both groups include three disulfide linkages connecting the Cys residues at positions 1 and 16, 8 and 20, and 15 and 28. As described in U.S. Pat. No. 5,051,403 (Miljanich et al.), the disulfide bridges are preferably formed by air oxidation of the full sequence peptide in the presence of dithiothreitol (DTT) without Cys-residue protection, but may also be formed by selective deprotection of each pair of Cys residues. This constraint excludes amino acid variations which prevent or otherwise hinder the formation of the three selected bridges.

Constraints 1 and 2 preserve the basic conformation of the OCT peptides imposed by the three disulfide bridges.

3. Within each of the two peptides groups, the residue positions which are invariant are most likely to be retained. Thus, for the G group peptides, the position 2 Lys, position 4 4Hyp, position 5 Gly, position 19 Ser, position 23 Tyr, and the position 26 Lys are retained, so that the G-group peptides have a total of 12 invariant residues (plus a deletion at position 18). Similarly, among the M-group peptides, the position 2 Lys, position 4 Lys, position 5 Gly, position 13 Tyr, position 14 Asp, position 18 Gly, position 19 Ser, position 22 Arg, position 25 Gly, and position 26 Lys are retained, for a total of 16 retained positions (plus deletions at positions 23 and 27). It is possible, of course, that invariant residues may be substituted by closely related amino acids, such as an Arg to Lys substitution, or a Tyr to Phe substitution.

4. Amino acids at positions not conserved by constraint 3 above, are "variant amino acids" and may be interchanged with other amino acids. In general, the variant amino acid at particular positions in an ω-conotoxin can be selected from same class amino acids, or their derivatives, or amino acids at analogous positions in homologous proteins in nature. Similarly, the variant amino acid may be chosen from same class amino acids of those variant amino acids at particular positions contained in the six sequences listed above. For example, if Leu occurs with high frequency at position 3 in related homologous proteins in nature, Leu, Ile, Val or other related amino acids and derivatives could be substituted at that position in an ω-conotoxin of the present invention. Likewise, for example, the Thr of position 17 of MVIIA (SEQ ID NO 2) may generally be substituted with Ser, Pro or 4Hyp.

5. If variants are found in both polar and nonpolar groups, the position is considered open to substitution. In the G-group peptides, these open positions are 10, 12, 13, and 21. In the M-group peptides, the open-substitution positions are 3, 11, and 12. The substitutions generally include L-amino acids.

6. Positions 25, 27, 29, or 30 of the G-group peptides may include a deletion. Positions 21, 23, or 24 of the M-group peptides may include a deletion.

7. The C-terminal amino acid residue of the peptide may be amidated.

The ω-conotoxins may be obtained by several processes known to those skilled in the art of peptide preparation. For example, they may be obtained from the biological source (*Conus molusks*) via harvest and purification techniques, by recombinant DNA techniques, or by synthetic routes. U.S. Pat. No. 4,447,356 (Olivera et al.) discloses an isolation and purification technique of ω-conotoxins from Conus species, the entire contents of which, are incorporated herein by reference. Solid phase and solution phase syntheses of the ω-conotoxins are disclosed in U.S. Pat. Nos. 5,432,155 (Olivera et al.), the entire contents of which, are incorporated herein by reference, and 5,051,403 (Miljanich et al.).

The ω-conotoxins of the present invention are intended for acute administration to a human patient. Preferably, the ω-conotoxins of the present invention will be administered intraocularly following traumatic and/or other acute ischemic events involving the retinal and optic nerve head tissues or prior to or during surgery to prevent ischemic damage or injury. While intraocular methods are preferred, topical ophthalmic, periocular or retrobulbar administration, of the ω-conotoxins is also contemplated by the present invention.

The ω-conotoxins of the present invention may be contained in various types of pharmaceutical compositions, in accordance with formulation techniques known to those skilled in the art. In general, the ω-conotoxins will be formulated in solutions for topical ophthalmic or intraocular or systemic administration. Solutions, suspensions and other dosage forms adapted for intraocular injection or perfusion, such as balanced salt solutions, are particularly preferred for the acute treatment of retinal and optic nerve head tissues.

When the ω-conotoxins of the present invention are administered during intraocular surgical procedures, such as through retrobulbar or periocular injection and intraocular perfusion or injection, the use of balanced salt irrigating solutions as vehicles are most preferred. BSS® Sterile Irrigating Solution and BSS Plus® Sterile Intraocular Irrigating Solution (Alcon Laboratories, Inc., Fort Worth, Tex., USA) are examples of physiologically balanced intraocular irrigating solutions. The latter type of solution is described in U.S. Pat. No. 4,550,022 (Garabedian et al.), the entire contents of which are hereby incorporated in the present specification by reference. Retrobulbar and periocular injections are known to those skilled in the art and are described in numerous publications including, for example, *Ophthalmic Surgery: Principles of Practice*, Ed., G. L. Spaeth, W. B. Sanders Co., Philadelphia, Pa., U.S.A., pages 85–87 (1990).

In general, the doses used for the above described purposes will vary, but will be in an effective amount to prevent, reduce or ameliorate acute retinal or optic nerve head tissue damage. As used herein, the term "pharmaceutically effective amount" refers to an amount of at least one ω-conotoxins which will reduce, prevent or ameliorate retinal or optic nerve head tissue damage in a human patient. The doses used for any of the above-described purposes will generally be from about 0.01 nanogram per milliliter (ng/ml) to about 1 microgram per milliliter (mg/ml) for intraocular infusion or injection. When the compositions are dosed topically, they will generally be in a concentration range of from 0.001 to about 5% w/v, with 1–2 drops administered 1–4 times per day.

As used herein, the term "pharmaceutically acceptable carrier" refers to any formulation which is safe, and provides the appropriate delivery for the desired route of administration of an effective amount of at least one compound of the present invention.

The invention in its broader aspects is not limited to the specific details shown and described above. Departures may be made from such details within the scope of the accompanying claims without departing from the principles of the invention and without sacrificing its advantages.

What is claimed is:

1. A method for the prevention or treatment of retinal or optic nerve head damage resulting from acute traumatic or acute ischemic events which comprises administering intraocularly to a human patient a composition comprising a pharmaceutically effective amount of at least one ω-conotoxin and a pharmaceutically acceptable carrier.

2. The method of claim 1, wherein the ω-conotoxin is selected from the group consisting of SEQ ID NOs 1–6.

3. The method of claim 2, wherein the composition is an intraocular injection formulation.

4. The method of claim 2, wherein the composition is an intraocular irrigating formulation.

5. The method of claim 1, wherein the ω-conotoxin is SEQ ID NO 1.

6. The method of claim 5, wherein the composition is an intraocular injection formulation.

7. The method of claim 5, wherein the composition is an intraocular irrigating formulation.

8. The method of claim 1, wherein the composition is an intraocular injection formulation.

9. The method of claim 1, wherein the composition is an intraocular irrigating formulation.

* * * * *